US00PP10566P

United States Patent [19]

Zary

[11] Patent Number: Plant 10,566

[45] Date of Patent: Aug. 25, 1998

[54] FLORIBUNDA ROSE PLANT NAMED 'JACYESP'

[75] Inventor: Keith W. Zary, Thousand Oaks, Calif.

[73] Assignee: Bear Creek Gardens, Inc., Medford, Oreg.

[21] Appl. No.: 800,049

[22] Filed: Feb. 14, 1997

[51] Int. Cl.[6] ..... A01H 5/00

[52] U.S. Cl. ..... Plt./24

[58] Field of Search ..... Plt./24

[56] References Cited

U.S. PATENT DOCUMENTS

P.P. 6,695 3/1989 Kordes ..... Plt./24

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the floribunda class, having attractive yellow flowers arranged in clusters; long stems; good vase life; good production; and moderate fragrance.

1 Drawing Sheet

The present invention relates to a new and distinct variety of rose plant of the floribunda class which was originated by me by crossing the variety INTERval, U.S. Plant Pat. No. 5648, with an unnamed yellow floribunda seedling.

The primary objective of this breeding was to produce a new rose variety having the long stems, good production, good vase life, fragrance and tendency to flower in clusters of the female parent combined with the clustering ability of the unnamed seedling male parent and its medium yellow flower color. The objective was substantially achieved, along with other desirable improvements, as evidenced by the following unique combination of characteristics that are outstanding in the new variety and that distinguish it from its parents, as well as from all other varieties of which I am aware:

1. Attractive yellow flowers arranged in clusters;
2. Long stems;
3. Good vase life;
4. Good production;
5. Moderate fragrance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—INTERval (U.S. Plant Pat. No. 5648).

*Pollen parent.*—Unnamed floribunda.

Classification:

*Botanical.*—Rosa hybrida.

*Commercial.*—Floribunda.

FLOWER

Observations made from specimens grown in a greenhouse environment at Somis, Calif. from March 1996 to January 1997.

Blooming habit: Recurrent.

Bud:

*Size.*—1 to 1¼ inches long when the petals start to unfurl.

*Form.*—The bud form is long, pointed ovoid.

*Color.*—When sepals first divide, bud color is Yellow-Orange Group 14C. When half blown, the upper sides of the petals are Yellow-Orange Group 14C fading to Yellow-Orange Group 14D on the outer petals, especially the edges of those petals; and the lower sides of the petals are Yellow-Orange Group 14C.

*Sepals.*—Color: Green Group 138C. Surface texture: Covered in fine hairs. There are three normally to heavily appendaged sepals. There are two unappendaged sepals with hairy edges.

*Receptacle.*—Color: Green Group 137C. Shape: Funnel. Size: Small (5/16×¼ inch). Surface: Smooth.

*Peduncle.*—Length: Short (2 inches to 2½ inches). Surface: Smooth. Color: Medium green. Strength: Stiff, erect.

Bloom:

*Size.*—Small. Average open size is 2½ to 3 inches.

*Borne.*—Several together, in clusters. Clusters: Flat to slightly rounded.

*Stems.*—Long, strong. Average length is about 18–22 inches.

*Form.*—When first open: High centered. Permanence: Flattens; all petals curl.

*Petalage.*—Number of petals under normal conditions: 30.

*Color.*—The upper sides of the petals are Yellow-orange Group 14C fading to Yellow-Orange Group 14D on flower edges. The reverse sides of the petals are Yellow-orange Group 14C. The base of each petal has a small (1/16×1/16 inch) deep yellow half moon at the point of attachment to the petal base. The major color on the upper side is Yellow-Orange Group 14C.

*Variegations.*—None.

*Discoloration.*—The general tonality at the end of the first day: No change. At the end of the third day: Slow change on the plant to Yellow-Orange 14C. Eventually, (day 5 or 6 on the plant) there is fading on the flower petal edges to Yellow-Orange Group 18D.

*Fragranc.*—Moderate.

Petals:

*Texture.*—Thick.

*Shape.*—Deltoid.

*Form.*—Tips slightly recurved; edges slightly quilled.

*Arrangement.*—Imbricated, with few petaloids in the center.

*Persistence.*—Petals drop off cleanly.

*Lastingness.*—On the plant: Long (7 days). As a cut flower: Long (11 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Yellowish white.

*Stigmas.*—Color: Greenish white.

Form: Bush.

Growth: Vigorous, upright, branching. Unpruned plant in the greenhouse after one year will be 6 to 6½ feet tall by 3 to 3½ feet wide. Plant will produce 160–170 stems per square meter of greenhouse.

Foliage:

*Number of leaflets on normal mid-stem leaves.*—5.

*Size.*—Medium (4½×3 inches).

*Quantity.*—Normal.

*Color.*—New foliage: Greyed-Orange Group 173A but very quickly turning green. Old foliage: Upper surface: Green Group 139A; lower surface: Green Group 136C.

Leaflets:

*Shape.*—Oval.

*Texture.*—Upper side: Leathery.

*Edge.*—Serrated.

*Serration.*—Single, small.

*Petiole rachis.*—Color: Green.

*Petiole underside.*—Smooth.

*Stipules.*—Short (½inch), serrated, bearded.

*Disease resistance.*—Resistant to mildew under normal growing conditions at Somis, Calif. Not tested for resistance to rust or blackspot.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Short (¼ inch), straight.

*Color when young.*—Green.

Small prickles:

*Quantity.*—On main stalks: None. On laterals: None.

I claim:

1. A new and distinct variety of rose plant of the floribunda class, substantially as herein shown and described, characterized particularly as to novelty by the unique combination of its attractive yellow flowers arranged in clusters; long stems; good vase life; good production; and moderate fragrance.

* * * * *

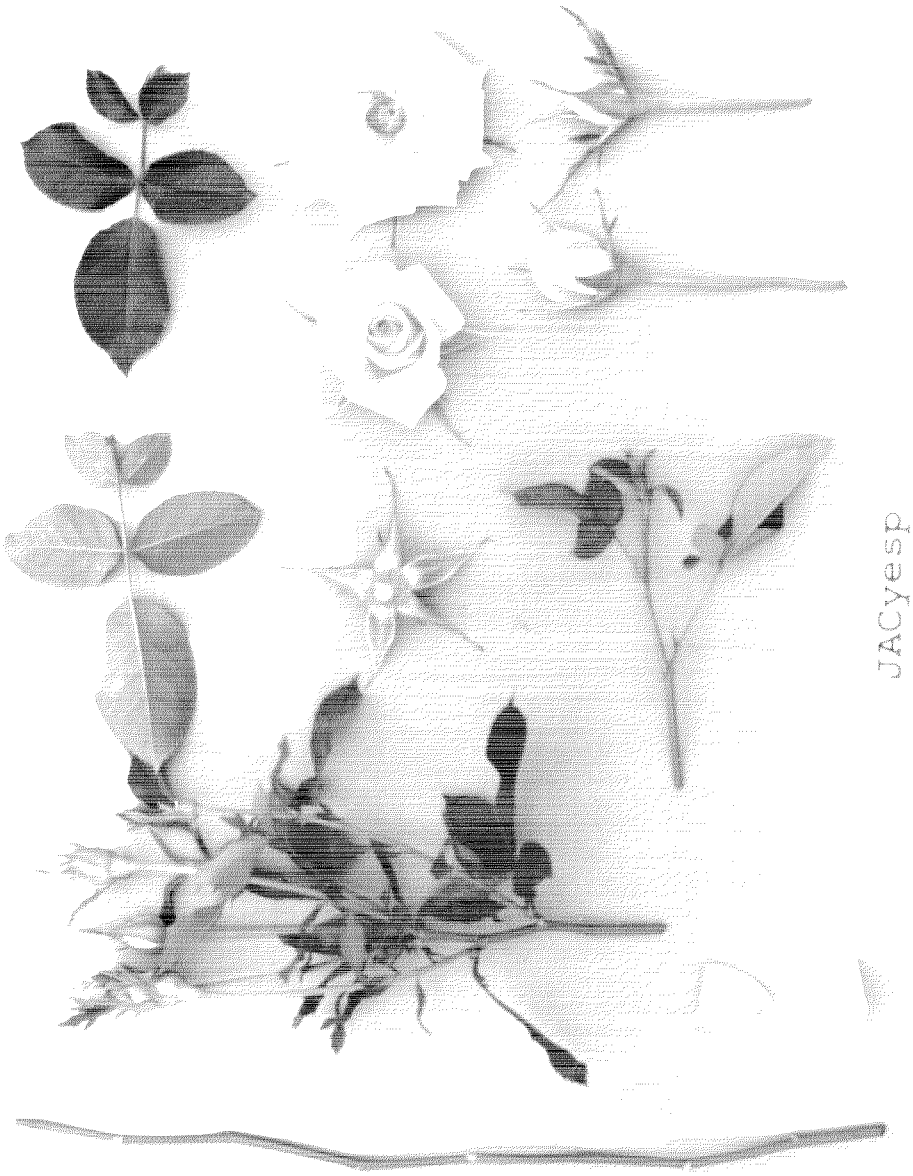
JACyesp